(12) United States Patent
Liu et al.

(10) Patent No.: US 10,190,100 B1
(45) Date of Patent: Jan. 29, 2019

(54) CHEMICAL MODIFICATION OF GLUCOSE OXIDASE AND ITS APPLICATION TO BIOSENSORS

(71) Applicant: Verily Life Sciences LLC, Mountain View, CA (US)

(72) Inventors: Zenghe Liu, Alameda, CA (US); Cindy Xiaoxin Zhou, San Jose, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 145 days.

(21) Appl. No.: 14/981,723

(22) Filed: Dec. 28, 2015

(51) Int. Cl.
*C12N 9/04* (2006.01)
*C12Q 1/00* (2006.01)
*G01N 27/327* (2006.01)
*G01N 27/416* (2006.01)

(52) U.S. Cl.
CPC ........... *C12N 9/0006* (2013.01); *C12Q 1/006* (2013.01); *G01N 27/3275* (2013.01); *G01N 27/4166* (2013.01); *C12Y 101/03004* (2013.01); *G01N 2333/904* (2013.01)

(58) Field of Classification Search
None
See application file for complete search history.

(56) References Cited

U.S. PATENT DOCUMENTS

| | | |
|---|---|---|
| 6,653,358 B2 | 11/2003 | Bruza |
| 7,731,835 B2 | 6/2010 | Buck |
| 8,080,385 B2 | 12/2011 | Heller |
| 8,385,998 B2 | 2/2013 | Zhang |
| 8,437,829 B2 | 5/2013 | Mao |
| 8,703,458 B2 | 4/2014 | Heller |
| 9,551,680 B2 * | 1/2017 | Liu ..................... G01N 27/327 |
| 2010/0300897 A1 | 12/2010 | Savage |
| 2011/0082356 A1 | 4/2011 | Yang et al. |
| 2011/0136929 A1 | 6/2011 | Chow |
| 2011/0152654 A1 | 6/2011 | Wang |
| 2012/0116191 A1 | 5/2012 | Markle |
| 2012/0245444 A1 | 9/2012 | Otis |
| 2012/0283537 A1 | 11/2012 | Petisce |
| 2013/0011460 A1 | 1/2013 | Liu |
| 2015/0001072 A1 | 1/2015 | Liu |

FOREIGN PATENT DOCUMENTS

| | | |
|---|---|---|
| CN | 102719423 | 10/2012 |
| WO | 2014210478 | 12/2014 |

OTHER PUBLICATIONS

International Search Report issued in connection with co-pending International Patent Application No. PCT/US2014/044608, ISA/KR dated Oct. 14, 2014, 6 pgs.
Written Opinion issued in connection with co-pending International Patent Application No. PCT/US2014/044608, ISA/KR dated Oct. 14, 2014, 5 pgs.
Gil, M.H., et al., "Immobilization of Glucose Oxidase on Thin-Film Gold Electrodes Produced by Magnetron Sputtering and Their Application in an Electrochemical Biosensor," Biotechnology Techniques, vol. 13, pp. 595-599 (1999).
Hall, C.E. et al., "Covalent Immobilisation of Glucose Oxidase on Methacrylate Copolymers for Use in an Amperometric Glucose Sensor," Analytica Chimica Acta, vol. 281, pp. 645-653 (1993).
Jusoh, Norhana et al., "Improvement of Glucose Biosensor Performances Using Poly(hydroxyethylmethacrylate) Outer Membrane," International Journal of Biology and Biomedical Engineering, Issue 1, vol. 6, pp. 77-86 (2012).
Slaughter, Gymama Ph.D., "Fabrication of Nanoindented Electrodes for Glucose Detection," Journal of Diabetes Science and Technology, vol. 4, Issue 2, pp. 320-327 (Mar. 2010).
Kang, Seong et al. "A sulfonamide based glucoseresponsive hydrogel with covalently immobilized glucose oxidase and catalase" Journal of Controlled Release, 86, p. 115-121 (Jan. 9, 2003) (Abstract).
Kang, E. T., et al. "Surface-Functionalized Polyaniline Films" J. Phys. Chem. B, 1997, 101 (50), pp. 10744-10750 (Dec. 11, 1997) (Abstract).
Li, Z. F. et al. "Covalent immobilization of glucose oxidase on the surface of polyaniline films graft copolymerized with acrylic acid" Biomaterials. Jan.-Feb. 1998;19(13): 45-53 (Abstract).

* cited by examiner

*Primary Examiner* — Anand U Desai
(74) *Attorney, Agent, or Firm* — McDonnell Boehnen Hulbert & Berghoff LLP

(57) ABSTRACT

A modified glucose oxidase for use in a sensor for the continuous or semi-continuous monitoring of glucose is disclosed. The modified glucose oxidase may include a glucose oxidase having at least one amino group substituted with a methacrylate through a hydrophilic linker including at least one alkylene oxide unit. A glucose sensor is also disclosed. The glucose sensor includes a crosslinked, hydrophilic copolymer sensing layer in contact with a surface of an electrode, where the sensing layer includes methacrylate-derived backbone chains covalently bound to glucose oxidase through a hydrophilic linker including at least one alkylene oxide unit. Also included is a method for making the modified glucose oxidase and the glucose sensor.

20 Claims, 4 Drawing Sheets

CHEMICAL MODIFICATION OF GLUCOSE OXIDASE AND ITS APPLICATION TO BIOSENSORS

BACKGROUND

Unless otherwise indicated herein, the materials described in this section are not prior art to the claims in this application and are not admitted to be prior art by inclusion in this section.

Glucose oxidase (GOx) is an oxido-reductase that catalyzes the oxidation of glucose to hydrogen peroxide and D-glucono-δ-lactone. Due to this property, GOx has been widely used to make biosensors to measure glucose for both in vitro and in vivo applications. For in vivo biosensors, the enzyme is typically immobilized onto the sensors. Immobilization can be accomplished by physically trapping the GOx in the biosensor or by chemically crosslinking the GOx in the biosensor.

Physically trapping the GOx in the sensor can be accomplished by initiating polymerization of a mixture including one or more polymerizable monomers and GOx. But this method suffers from the low solubility of GOx in the formulation and by the slow leaching out of the GOx from the resulting polymer matrix. Chemical crosslinking can be accomplished by reacting glutaraldehyde with the free amine groups on GOx. But glutaraldehyde-bound GOx sensors are hindered by the toxicity of glutaraldehyde and a loss of enzymatic activity of the GOx.

SUMMARY

In one aspect, a modified glucose oxidase is disclosed. The modified glucose oxidase may include a glucose oxidase wherein at least one amino group is substituted with a methacrylate through a hydrophilic linker. The linker may include alkylene oxide-derived units.

In another aspect, a glucose sensor is disclosed. The glucose sensor includes a crosslinked, hydrophilic copolymer sensing layer in contact with a surface of an electrode. The copolymer sensing layer includes backbone chains having first methacrylate-derived units and second methacrylate-derived units. Each first methacrylate-derived unit is covalently bound to glucose oxidase through a hydrophilic linker, and the second methacrylate-derived units in different backbone chains are connected to one another by hydrophilic crosslinks, resulting in interconnected polymer chains. The sensor has third methacrylate-derived monomeric units, each having a hydrophilic side chain, present in the sensing layer or in a protective membrane provided on the sensing layer. The protective membrane is a crosslinked, hydrophilic copolymer having backbone chains of third methacrylate-derived monomeric units and fourth methacrylate-derived units, where the fourth methacrylate-derived units in different backbone chains are connected to one another by hydrophilic crosslinks.

In another aspect, a method for forming a glucose sensor is disclosed. The formation of the sensing layer can include forming a mixture including the precursor components of the sensing layer, depositing the mixture onto a surface of an electrode, and curing the deposited mixture. The mixture can include a methacrylate monomer covalently bound to glucose oxidase through a hydrophilic linker, a dimethacrylate monomer, and an initiator. A methacrylate monomer having a hydrophilic side chain can be included in the mixture, or is included in a protective membrane provided on the sensing layer. The protective membrane can be formed by forming a mixture that includes a methacrylate monomer having a hydrophilic side chain, a dimethacrylate monomer and an initiator, depositing the mixture onto the sensing layer, and curing the deposited mixture.

These as well as other aspects, advantages, and alternatives, will become apparent to those of ordinary skill in the art by reading the following detailed description, with reference where appropriate to the accompanying drawings.

DETAILED DESCRIPTION

Figure 1:
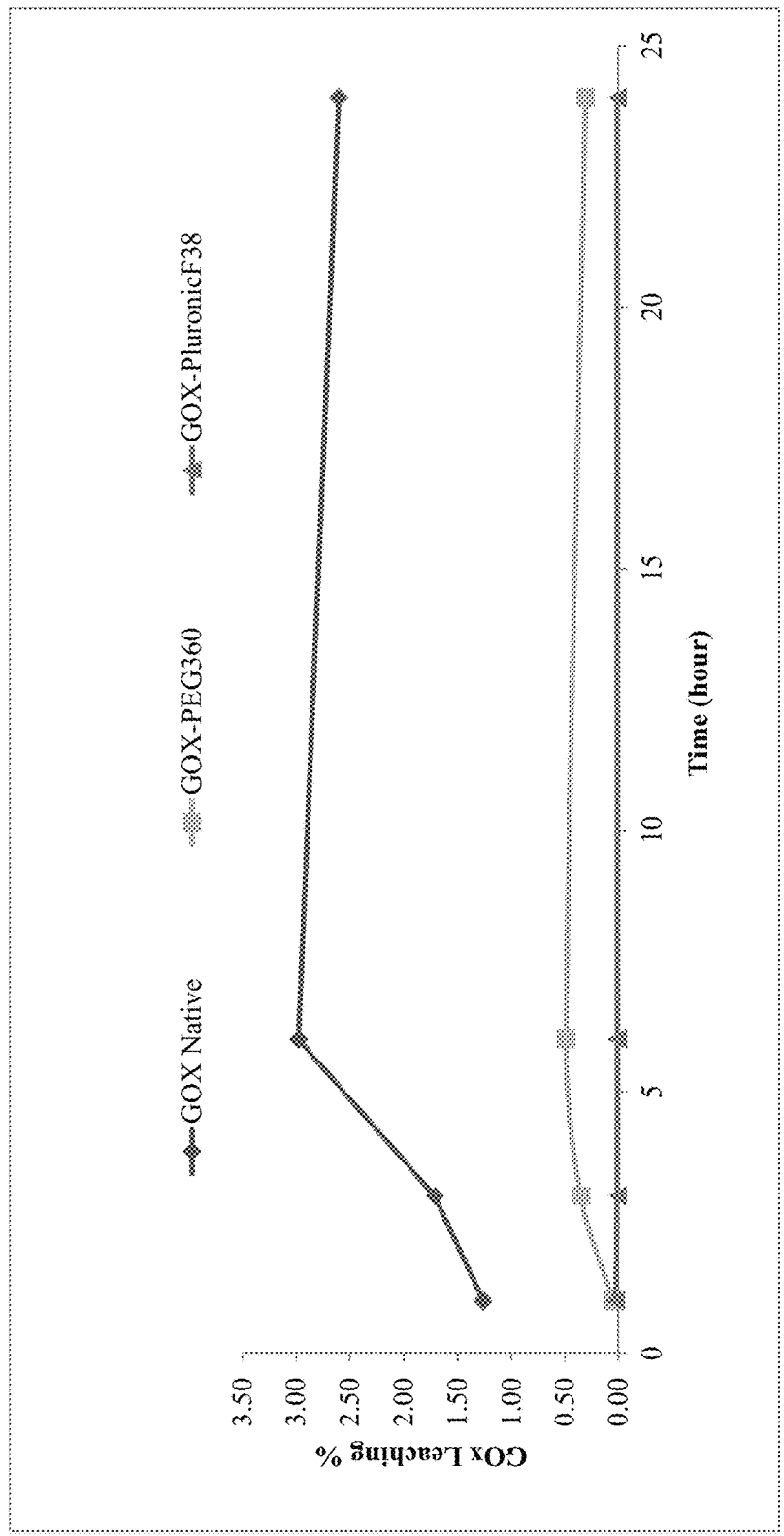
FIG. 1 is a comparison of GOx release from three hydrogel membranes made with Native GOx, Methacrylate-PluronicF38-GOx and Methacrylate-PEG360-GOx.

The method and system embodiments described herein are not meant to be limiting. It will be readily understood that certain aspects of the disclosed methods and systems can be arranged and combined in a wide variety of different configurations, all of which are contemplated herein.

In one aspect, a modified glucose oxidase is disclosed. The modified glucose oxidase may include a glucose oxidase wherein at least one amino group is substituted with a methacrylate through a hydrophilic linker. The linker may include alkylene oxide-derived units. In some embodiments, the modified glucose can have the structure of formula (I):

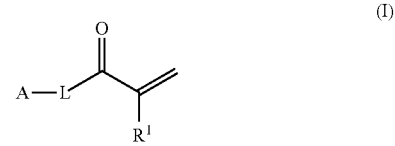

where A is glucose oxidase, L is a hydrophilic linker and $R^1$ is hydrogen or $-C_1-C_6$alkyl. L can be water soluble or soluble in a water-miscible solvent, such as an alcohol. In some examples, L can have one or more heteroatoms, for example, nitrogen, oxygen or sulfur atoms. In some embodiments, L can have a reactive group capable of forming a covalent bond with a reactive group of A.

In some embodiments, $R^1$ is hydrogen or $-C_1-C_3$alkyl. In other embodiments, $R^1$ is hydrogen, methyl or ethyl. In some examples, $R^1$ is hydrogen or methyl. In other examples $R^1$ is hydrogen, while in other examples, $R^1$ is methyl.

In some embodiments, L includes one or more alkylene oxide units. The alkylene oxide units can be derived from ethylene oxide, propylene oxide or butylene oxide, and can be a combination of two or three different alkylene oxide units. In some embodiments, the alkene oxide units form a poly(alkylene oxide) such as poly(ethylene oxide) or poly(propylene oxide).

In certain embodiments, L can be $-L^1-L^2-L^3-$, where each of $L^1$, $L^2$ and $L^3$ can be independently absent or an alkylene oxide unit, where at least one of $L^1$, $L^2$ and $L^3$ is an alkylene oxide unit, and where at least one of $L^1$, $L^2$ and $L^3$ includes a reactive group capable of forming a covalent bond with a reactive group of A.

$L^1$, $L^2$ or $L^3$ can include a reactive group that can undergo chemical reaction with one or more reactive groups of glucose oxidase to form a covalent bond. The linker reactive groups can include carboxylate, activated ester, acid chloride, or any other group capable of reacting with a hydroxyl, thiol or amino group of glucose oxidase or a derivative thereof, such as the amino group of a lysine amino acid residue. For example, in some embodiments, the modified glucose can have the structure of formula (Ia):

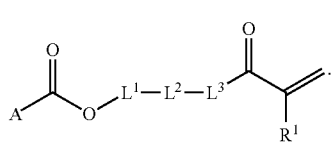

In some embodiments, $L^1$, $L^2$ and $L^3$ each include one or more alkylene oxide-derived units. For example, $L^1$, $L^2$ and $L^3$ may be independently selected from poly(ethylene oxide), poly(propylene oxide) and poly(butylene oxide). In other embodiments, $L^1$, $L^2$ and $L^3$ may be independently selected from poly(ethylene oxide) and poly(propylene oxide).

In some embodiments, L, $L^2$ and $L^3$, either individually or combined, have a number average molecular weight ($M_n$) of about 100 to about 10,000. In certain embodiments, $L^1$, $L^2$ and $L^3$ are selected so that the $M_n$ of $L^1$, $L^2$ and $L^3$, either individually or combined, falls within a range in Table 1.

TABLE 1

$M_n$ range of the poly(alkylene oxide) portion of the modified glucose (values are approximate).

| Low | High |
|---|---|
| 100 | 200 |
| 200 | 300 |
| 300 | 400 |
| 400 | 500 |
| 500 | 600 |
| 600 | 700 |
| 700 | 800 |
| 800 | 900 |
| 900 | 1,000 |
| 1,000 | 2,000 |
| 2,000 | 3,000 |
| 3,000 | 4,000 |
| 4,000 | 5,000 |
| 5,000 | 6,000 |
| 7,000 | 8,000 |
| 8,000 | 9,000 |
| 9,000 | 10,000 |

For example, in some embodiments, the modified glucose can have the structure of formula (Ib):

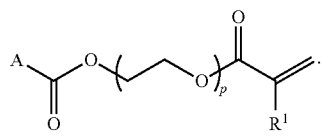

where p is 1-100; $R^1$ is hydrogen or —$C_1$-$C_6$alkyl; and A is glucose oxidase. In some embodiments, p is such that the number average molecular weight ($M_n$) of the PEG portion (within the brackets in formula (Ib)) of the modified glucose is about 100 to about 10,000. For example, p can be selected such that the $M_n$ of the PEG portion of the modified glucose falls within a range in Table 1. For example, p may be selected such that the $M_n$ of the PEG portion of the modified glucose falls within the range of about 300 to about 400.

In other embodiments, the modified glucose can have the structure of formula (Ic):

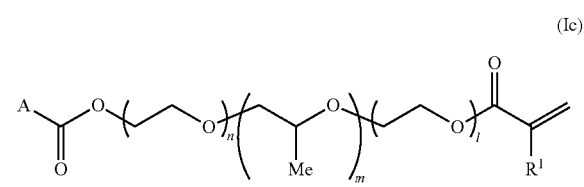

where n is 1-50; m is 1-100; 1 is 1-50; $R^1$ is hydrogen or —$C_1$-$C_6$alkyl; and A is glucose oxidase. In some embodiments, n is 10-20; m is 30-50; and l is 1-50.

In some embodiments, n, m and 1 are such that the number average molecular weight ($M_n$) of the alkylene oxide portion (within the three sets of brackets in formula (Ic)) of the modified glucose is about 100 to about 10,000. For example, n, m and l can be selected such that the $M_n$ of the alkylene oxide portion of the modified glucose falls within a range in Table 1. For example, n, m and 1 may be selected such that the $M_n$ of the alkylene oxide portion of the modified glucose falls within the range of about 4,000 to about 5,000.

In another aspect, a method for making a modified glucose is disclosed. The method can involve reacting glucose oxidase with an activated methacrylate. The activated methacrylate may have a hydrophilic linker between the activated group (i.e., the group that undergoes covalent bond formation with glucose oxidase) and the methacrylate group. In some embodiments, the hydrophilic linker is such that a modified glucose of any of formulae (I) or (Ia)–(Ic) is provided. For example, the method can include reacting glucose oxidase with a compound having the structure of formula (I'):

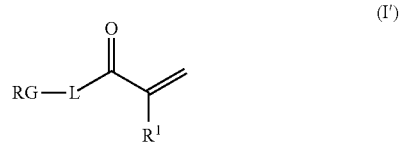

where RG is a reactive group and $R^1$ is as described above. The reactive group can be any group capable of forming a covalent bond with glucose oxidase. Reactive groups can include carboxylate, activated ester, acid chloride, or any other group capable of reacting with a hydroxyl, thiol or amino group of glucose oxidase or a derivative thereof, such as the amino group of a lysine amino acid residue.

In another embodiment, the method can include reacting glucose oxidase with a compound having the structure of formula (Ia'):

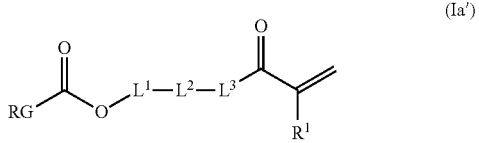

(Ia′)

where RG is a reactive group, and $L^1$, $L^2$, $L^3$ and $R^1$ are as described above.

In another embodiment, the method can include reacting glucose oxidase with a compound having the structure of formula (Ib′):

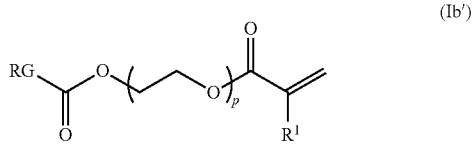

(Ib′)

where RG is a reactive group, and p and $R^1$ are as described above.

In another embodiment, the method can include reacting glucose oxidase with a compound having the structure of formula (Ic′):

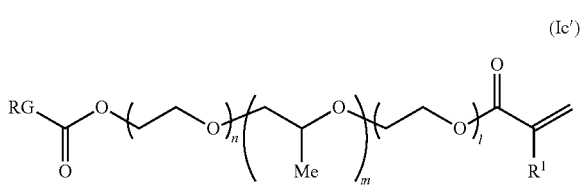

(Ic′)

where RG is a reactive group, and n, m, l and $R^1$ are as described above.

The amount of glucose oxidase amino groups covalently bound to a methacrylate (i.e., degree of modification) depends on the stoichiometric ratio of the native glucose oxidase to activated methacrylate used, as well as other variables in the modification reaction. In some embodiments, about 25% to about 100% of the amino groups on the modified glucose oxidase are covalently bound to the methacrylate. In other embodiments about 25% to about 50%, or about 25% to about 40%, or about 50% to about 75%, about 50% to about 90%, or about 30% to about 60%, or about 30% to about 70%, or about 40% to about 80%, or about 40% to about 60% of the of glucose oxidase amino groups are modified.

In another aspect, a glucose sensor is disclosed. The glucose sensor includes:
a sensing layer in contact with a surface of an electrode, wherein the sensing layer includes:
  backbone chains including
    first methacrylate-derived monomeric units, each of which is covalently bound to glucose oxidase through a hydrophilic linker including at least one alkylene oxide unit,
    second methacrylate-derived monomeric units, and
    optionally, third methacrylate-derived monomeric units, each having a hydrophilic side chain,
  hydrophilic crosslinks between the second methacrylate-derived monomeric units in different backbone chains; and optionally, an additional layer provided on the sensing layer including third methacrylate-derived monomeric units, each having a hydrophilic side chain,
wherein the third methacrylate-derived monomeric units are present in at least one of the additional layer or the backbone chains of the sensing layer.

In some embodiments, the glucose sensor can be an enzyme-based biosensor. This device is able to convert a glucose-concentration-dependent biochemical reaction signal into a measurable physical signal, such as an optical or electrical signal. The biosensor can be used in the detection of glucose in clinical, environmental, agricultural and biotechnological applications. The detection of glucose in biological fluids, such as blood, tear film, or intestinal fluid, can be important in the diagnosis and the monitoring of many diseases.

In some embodiments, the glucose sensor can be a component of a body-mountable device, such as an eye-mountable, tooth-mountable, or skin-mountable device. The eye-mountable device can be configured to monitor health-related information based on glucose detected in a tear film (the term "tear film" is used herein interchangeably with "tears" and "tear fluid") of a user wearing the eye-mountable device. For example, the eye-mountable device can be in the form of a contact lens that includes a sensor configured to detect glucose. The eye-mountable device can also be configured to monitor various other types of health-related information.

In some embodiments, the body-mountable device may include a tooth-mountable device. The tooth-mountable device may take the form of or be similar in form to the eye-mountable device, and be configured to detect glucose in a fluid (e.g., saliva) of a user wearing the tooth-mountable device.

In some embodiments, the body-mountable device may include a skin-mountable device. The skin-mountable device may take the form of or be similar in form to the eye-mountable device, and be configured to detect glucose in a fluid (e.g., perspiration, blood, interstitial fluid, etc.) of a user wearing the skin-mountable device.

The sensor as described herein can include one or more conductive electrodes through which current can flow. Depending on the application, the electrodes can be configured for different purposes. For example, a sensor can include a working electrode, a reference electrode, and a counter-electrode. Also possible are two-electrode systems, in which the reference electrode serves as a counter-electrode. The working electrode can be connected to the reference electrode via a circuit, such as a potentiostat.

The electrode can be formed from any type of conductive material and can be patterned by any process that be used for patterning such materials, such as deposition or photolithography, for example. The conductive materials can be, for example, gold, platinum, palladium, titanium, carbon, copper, silver/silver-chloride, conductors formed from noble materials, metals, or any combinations of these materials. Other materials can also be envisioned.

The sensing layer of the glucose sensor can be a cross-linked, hydrophilic copolymer that includes backbone chains of first and second methacrylate-derived units and optionally third methacrylate-derived monomeric units. The first methacrylate-derived units of the backbone chains are each covalently bound to glucose oxidase through a hydrophilic linker. Each of the second methacrylate-derived units is covalently bound through a hydrophilic linker to another second methacrylate-derived unit in a different backbone chain. The crosslinks, or groups through which the second methacrylate-derived units of different backbone chains are connected to each other, are discussed in greater detail below. The optional third methacrylate-derived monomeric units each have a hydrophilic side chain. Various conformations and compositions of the linkers of the first methacrylate-derived units, and the crosslinks of the second methacrylate-derived units, and the side chains of the third methacrylate-derived units can be used to adjust the properties of the crosslinked, hydrophilic copolymer as desired, which include hydrophilicity, permeability and the ability to immobilize glucose oxidase.

The sensor can also include a protective membrane provided on the sensing layer. For example, the protective membrane may be provided when the sensing layer lacks the third methacrylate-derived monomeric units. The protective membrane can be a crosslinked, hydrophilic copolymer having backbone chains of third and fourth methacrylate-derived monomeric units. Each of the third methacrylate-derived monomeric units have a hydrophilic side chain, and each of the fourth methacrylate-derived units are covalently bound through a hydrophilic linker to another fourth methacrylate-derived unit in a different backbone chain. The linkers, or groups through which the fourth methacrylate-derived units of different backbone chains are connected to each other, are herein referred to as "crosslinks".

The first methacrylate-derived units can be derived from the modified glucose described above. In some embodiments, the first methacrylate-derived units can have the structure of formula (II):

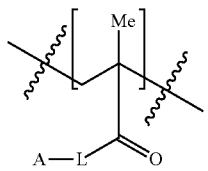

(II)

where L is a hydrophilic linker and A is glucose oxidase. L can be water soluble or soluble in a water-miscible solvent, such as an alcohol. In some examples, L can have one or more heteroatoms, for example, nitrogen, oxygen or sulfur atoms. In some embodiments, L can have a reactive group capable of forming a covalent bond with a reactive group of A.

In some embodiments, L includes one or more alkylene oxide units. The alkylene oxide units can be derived from ethylene oxide, propylene oxide or butylene oxide, and can be a combination of two or three different alkylene oxide units. In some embodiments, the alkene oxide units form a poly(alkylene oxide) such as poly(ethylene oxide) or poly(propylene oxide).

In certain embodiments, L can be -$L^1$-$L^2$-$L^3$-, where each of $L^1$, $L^2$ and $L^3$ can be absent or an alkylene oxide unit, wherein at least one of $L^1$, $L^2$ and $L^3$ is an alkylene oxide unit and where at least one of $L^1$, $L^2$ and $L^3$ includes a reactive group capable of forming a covalent bond with a reactive group of A. For example, in some embodiments, the first methacrylate-derived units can have the structure of formula (IIa):

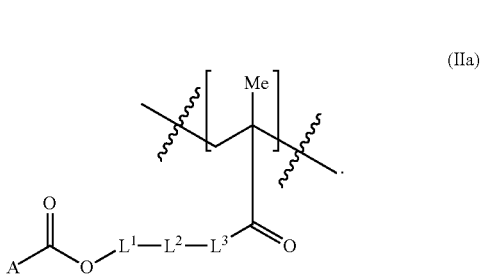

(IIa)

$L^1$, $L^2$ or $L^3$ can include a reactive group that can undergo chemical reaction with one or more reactive groups of glucose oxidase to form a covalent bond. The linker reactive groups can include carboxylate, activated ester, acid chloride, or any other group capable of reacting with a hydroxyl, thiol or amino group of glucose oxidase or a derivative thereof, such as the amino group of a lysine amino acid residue.

In some embodiments, $L^1$, $L^2$ and $L^3$ each include one or more alkylene oxide-derived units. For example, $L^1$, $L^2$ and $L^3$ may be independently selected from poly(ethylene oxide), poly(propylene oxide) and poly(butylene oxide). In other embodiments, $L^1$, $L^2$ and $L^3$ may be independently selected from poly(ethylene oxide) and poly(propylene oxide). For example, in some embodiments, the first methacrylate-derived units can have the structure of formula (IIb):

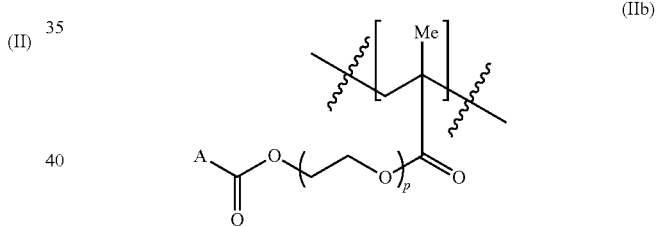

(IIb)

where p is 1-100; $R^1$ is hydrogen or —$C_1$-$C_6$alkyl; and A is glucose oxidase.

In other embodiments, the first methacrylate-derived units can have the structure of formula (IIc):

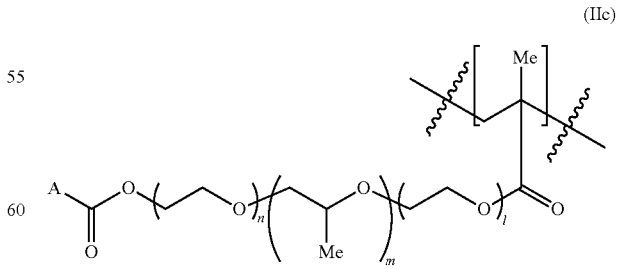

(IIc)

where n is 1-50, m is 1-100 and l is 1-50.

In some embodiments, the third methacrylate-derived units can have the structure of formula (III):

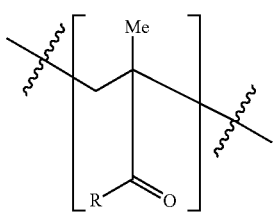

(III)

where R is a hydrophilic group. R can be water soluble or soluble in a water-miscible solvent, such as an alcohol. In some examples, R can have one or more heteroatoms, for example, nitrogen, oxygen or sulfur atoms. In some embodiments, L can have one or more hydroxy groups.

In some embodiments, R includes one or more alkylene oxide units. The alkylene oxide units can be derived from ethylene oxide, propylene oxide or butylene oxide, and can be a combination of two or three different alkylene oxide units. In some embodiments, the alkene oxide units form a poly(alkylene oxide) such as poly(ethylene oxide) or poly(propylene oxide).

In some embodiments, the third methacrylate-derived units can have the structure of formula (IIIa):

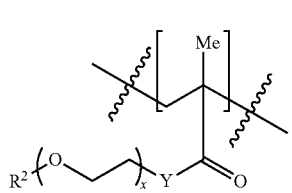

(IIIa)

where Y is —O—, —NR'— or —S—; x is 1, 2, 3, 4, 5, 6, 7, 8, 9 or 10; and $R^2$ is hydrogen, —$C_1$-$C_{12}$alkyl, —$C_1$-$C_{12}$alkyl-OH, —$SIR'_3$, —C(O)—$C_1$-$C_{12}$alkyl, —$C_1$-$C_{12}$alkyl-C(O)OR', where R' is hydrogen or —$C_1$-$C_{12}$alkyl.

In certain embodiments, the third methacrylate-derived units have the structure:

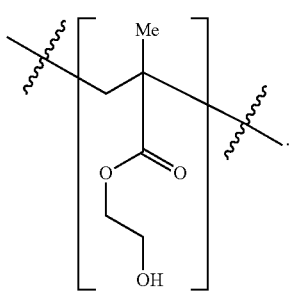

.

In some embodiments, the third methacrylate-derived units can have the structure of formula (IIIb):

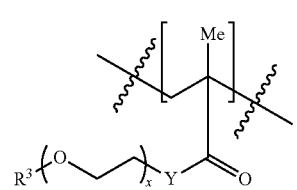

(IIIb)

where Y is —O—, —NR'— or —S—; x is an average value of from about 2 to about 250; and $R^3$ is hydrogen, —$C_1$-$C_{12}$alkyl, —$SIR'_3$, —C(O)—$C_1$-$C_{12}$alkyl, —$C_1$-$C_{12}$alkyl-C(O)OR', where R' is hydrogen or —$C_1$-$C_{12}$alkyl.

In some embodiments, the third methacrylate-derived units can have the structure of formula (IIIb), where Y and $R^3$ are as described above and x is such that the poly(ethylene oxide) has a number average molecular weight ($M_n$) of about 100 to about 10,000. In certain embodiments, x is selected so that the $M_n$ of the poly(ethylene oxide) falls within a range in Table 2.

TABLE 2

$M_n$ range of the poly(ethylene oxide) portion of the third methacrylate-derived units (values are approximate).

| Low | High |
| --- | --- |
| 100 | 200 |
| 200 | 300 |
| 300 | 400 |
| 400 | 500 |
| 500 | 600 |
| 600 | 700 |
| 700 | 800 |
| 800 | 900 |
| 900 | 1,000 |
| 1,000 | 2,000 |
| 2,000 | 3,000 |
| 3,000 | 4,000 |
| 4,000 | 5,000 |
| 5,000 | 6,000 |
| 7,000 | 8,000 |
| 8,000 | 9,000 |
| 9,000 | 10,000 |

In certain embodiments, the glucose sensor has third methacrylate-derived units having the structure of formula (IIIb), where Y is —O—, $R^3$ is methyl, and x is such that the poly(ethylene oxide) portion has a number average molecular weight ($M_n$) of about 500.

The crosslinks of the sensing layer and/or protective membrane are groups through which the second and/or fourth methacrylate-derived units of different backbone chains are connected to each other, and are represented by "W" in formula (IV):

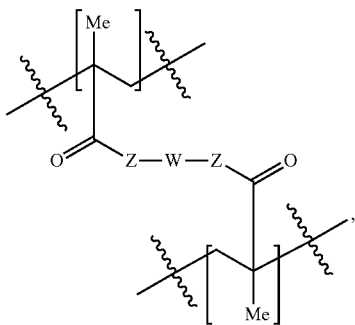

(IV)

where Z is independently —O—, —NR'— or —S—; and W is a hydrophilic group.

In some embodiments, the crosslinks are hydrophilic. The crosslinks can be soluble in water or a water-miscible solvent, such as an alcohol. The crosslinks can have one or more heteroatoms, for example, nitrogen, oxygen or sulfur atoms. In some embodiments, the crosslinks have one or more hydroxy groups.

In some embodiments, the crosslinks include one or more alkylene oxide units. The alkylene oxide units can be in the form of a polymer, such as poly(ethylene oxide), poly(propylene oxide), poly(butylene oxide) or a mixture thereof, and can be a copolymer including a combination of two or three different alkylene oxide units. In some embodiments, the poly(alkylene oxide) of the crosslinks is a block copolymer including blocks of two or three different poly(alkylene oxide) polymers. In certain embodiments, the poly(alkylene oxide) is a block copolymer of poly(ethylene oxide) and poly(propylene oxide). In other embodiments, the crosslinks include poly(ethylene oxide).

In some embodiments, the crosslinks include one or more ethylene oxide units. For example, the crosslinks (e.g., W in formula (IV) above) can have the structure of formula (IIIa):

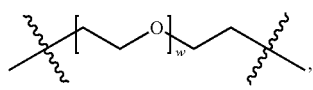

(IVa)

where w is 1, 2, 3, 4, 5, 6, 7, 8, 9 or 10.

In certain embodiments, w is an average value of from about 2 to about 250.

In other embodiments, w in the crosslinks of formula (IVa) is such that the number average molecular weight ($M_n$) of the PEG portion (within the brackets in formula (IVa)) of the crosslinks is about 100 to about 10,000. For example, w can be selected such that the $M_n$ of the PEG portion of the crosslinks falls within a range in Table 3:

TABLE 3

| $M_n$ range of the PEG portion of the crosslinks (values are approximate). | |
|---|---|
| Low | High |
| 100 | 200 |
| 200 | 300 |
| 300 | 400 |
| 400 | 500 |
| 500 | 600 |

TABLE 3-continued

| $M_n$ range of the PEG portion of the crosslinks (values are approximate). | |
|---|---|
| Low | High |
| 600 | 700 |
| 700 | 800 |
| 800 | 900 |
| 900 | 1,000 |
| 1,000 | 2,000 |
| 2,000 | 3,000 |
| 3,000 | 4,000 |
| 4,000 | 5,000 |
| 5,000 | 6,000 |
| 7,000 | 8,000 |
| 8,000 | 9,000 |
| 9,000 | 10,000 |

In some embodiments, the crosslinks are derived from di(ethylene glycol) dimethacrylate, i.e., compounds of formula (IV) or (IVa) where Z is —O— and w is 1.

In some embodiments, the presence of the hydrophilic side chains of the third methacrylate-derived units in the sensing layer can form a porous network. The structure of the porous network includes regions within the copolymer that are not occupied by polymer. These regions are referred to herein as "pores" or "voids".

Similarly, when the sensor includes a protective membrane with third methacrylate-derived units, the hydrophilic side chains of the third methacrylate-derived units in the protective membrane can provide a protective membrane having a porous network.

The porous network of the protective membrane or the porous network formed in the sensing layer by the third methacrylate-derived units can facilitate control of the equilibrium between the concentration of glucose in the sample solution, and the glucose concentration in the proximity of the glucose sensor electrode surface. When all of the glucose arriving at the glucose sensor is consumed, the measured output signal can be linearly proportional to the flow of the glucose and thus to the concentration of the glucose. However, when the glucose consumption is limited by the kinetics of chemical or electrochemical activities in the glucose sensor, the measured output signal may no longer be controlled by the flow of glucose and may no longer be linearly proportional to the flow or concentration of the glucose. In this case, only a fraction of the glucose arriving at the glucose oxidase is consumed before the sensor becomes saturated, whereupon the measured signal stops increasing, or increases only slightly, with an increasing concentration of glucose. The porous network can reduce the flow of the glucose to the glucose oxidase so the sensor does not become saturated and can therefore enable a wider range of glucose concentrations to be measured.

The hydrophilic properties of the side chain of the third methacrylate-derived units can be varied to produce desired properties of the porous network, such as permeability of glucose. For example, flow of glucose into or across the sensor can be dependent on multiple factors, and thus, the porous network can be altered to obtain a sensor with specific properties for monitoring glucose. In some applications, the hydrophilicity of the porous network can be adjusted by changing the number alkylene oxide units in the side chain of the third methacrylate-derived units. Similarly, the hydrophilicity of the porous network can be adjusted by modifying the ratio of carbon atoms (i.e., —C—, —CH—, —CH$_2$— or —CH$_3$) to alkylene oxide units in the third methacrylate-derived units.

In some embodiments, the glucose sensor may include a copolymer including glucose oxidase ("GOx") located on the working electrode to catalyze a reaction with glucose to produce hydrogen peroxide ($H_2O_2$). As shown below, the hydrogen peroxide can then be oxidized at the working electrode to releases electrons to the working electrode, which generates a current.

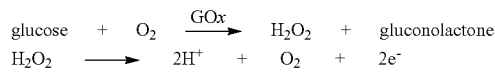

The current generated by either reduction or oxidation reactions can be approximately proportionate to the reaction rate. Further, the reaction rate can be dependent on the rate of glucose molecules reaching the electrochemical sensor electrodes to fuel the reduction or oxidation reactions, either directly or catalytically through a reagent. In a steady state, where glucose molecules diffuse to the electrochemical sensor electrodes from a sampled region at approximately the same rate that additional glucose molecules diffuse to the sampled region from surrounding regions, the reaction rate can be approximately proportionate to the concentration of the glucose molecules. The current can thus provide an indication of the glucose concentration.

The thickness of the crosslinked, hydrophilic copolymer of the glucose sensor can vary depending on the desired properties of the glucose sensor, and whether a protective membrane is included. The thickness of the copolymer, as measured from the top of electrode to the top of the copolymer (or membrane), can play an important role in regulating the flow of glucose to the glucose oxidase. Depending on the characteristics of the methacrylate-derived units in the copolymer, the thickness of the copolymer can be from less than about 10 μm to about 30 μm. In some instances, the copolymer is less than 20 μm in thickness, where in other applications the copolymer is about 20 μm to about 25 μm in thickness. In certain applications, the copolymer is about 10 μm to about 15 μm in thickness, where in other applications the copolymer is about 15 μm to about 20 μm or about 25 μm to about 30 μm in thickness. In some embodiments, the copolymer is about 20 μm in thickness.

In another aspect, a method for making a glucose sensor is disclosed. The method can involve forming a crosslinked, hydrophilic copolymer sensing layer on a surface of an electrode, and optionally forming a crosslinked, hydrophilic copolymer protective membrane on the sensing layer. The method includes the formation of the sensing layer, including:
  a) forming a first mixture including a first methacrylate monomer, a first dimethacrylate monomer, and a first initiator, where the first methacrylate monomer includes a covalent bond to glucose oxidase through a hydrophilic linker comprising at least one alkylene oxide unit;
  b) depositing the first mixture on a surface of an electrode;
  c) curing the first mixture to provide a sensing layer; and including a second methacrylate monomer in at least one of the first mixture or a second mixture deposited on the sensing layer.

In some embodiments of the method, the first mixture includes the second methacrylate monomer. In other embodiments, the second mixture includes the second methacrylate monomer.

In some embodiments of the method, the method further involves:
  a) forming a second mixture including the second methacrylate monomer, a second dimethacrylate monomer, and a second initiator;
  b) depositing the second mixture onto the sensing layer; and
  c) curing the deposited second mixture to provide a protective membrane on the sensing layer.

The ratios of the combined components in the sensing layer and/or protective membrane can vary depending on the desired properties of the resulting glucose sensor. For example, adjusting the type and/or amount of first or second dimethacrylate monomer can alter the porous network of the resulting crosslinked, hydrophilic copolymer. Controlling the properties of the porous network can allow for the tuning of the permeability of the glucose sensor. Similar tunability can also be accomplished by adjusting the amount of the first and/or second mixtures deposited on the electrode and/or the sensing layer during the formation of the sensing layer and protective membrane, respectively.

The first and/or second mixture can be formed in an aqueous medium, alcoholic medium, or mixture thereof. The aqueous medium can include a buffered aqueous solution, such as, for example, a solution containing citric acid, acetic acid, borate, carbonate, bicarbonate, 4-2-hydroxyethyl-1-piperazineethanesulfonic acid (HEPES), 3-{[tris(hydroxymethyl)methyl]amino}propanesulfonic acid (TAPS), N,N-bis(2-hydroxyethyl)glycine (Bicine), tris(hydroxymethyl)methylamine (Tris), N-tris(hydroxymethyl)methylglycine (Tricine), 3-[N-Tris(hydroxymethyl)methylamino]-2-hydroxypropanesulfonic acid (TAPSO), 2-{[tris(hydroxymethyl)methyl]amino}ethanesulfonic acid (TES), 3-(N-morpholino)propanesulfonic acid (MOPS), piperazine-N,N'-bis(2-ethanesulfonic acid) (PIPES), dimethylarsinic acid (Cacodylate), saline sodium citrate (SSC), 2-(N-morpholino)ethanesulfonic acid (MES), 2(R)-2-(methylamino) succinic acid, or phosphate buffered saline (PBS). In some embodiments, the mixtures are formed in a mixture of a buffered aqueous solution and ethanol.

In some embodiments of the method, the percentage of each component in the first and/or second mixture can be varied. In some instances, the percentage of the first monomer in the formation of the sensing layer is about 1% by weight to about 50% by weight, and the percentage of second methacrylate monomer is about 50% by weight to about 98% by weight. All percentages are given as a percentage of the cumulative amount of first monomer and second monomer in the mixture. For example, in certain examples, the percentage of the first methacrylate monomer is about 10%, and the amount of second methacrylate monomer is about 90%. The percentage of the first dimethacrylate monomer in the formation of the sensing layer, and/or percentage of the second dimethacrylate monomer in the formation of the protective membrane is about 0.1% by weight to about 15% by weight. The percentage of the first initiator in the formation of the sensing layer, and/or the percentage of the second initiator in the formation of the protective membrane is about 0.1% by weight to about 1% by weight. In certain embodiments, the first and/or second mixture is thoroughly mixed, optionally with a stirrer or shaker, before being deposited onto a surface of an electrode.

In some embodiments of the method, the first mixture can be formed by combining individual solutions having the components of the mixture. For example, the method can involve:

a) forming a first solution including the first methacrylate monomer, first dimethacrylate monomer, and first initiator;
b) forming a second solution including the second methacrylate monomer, first dimethacrylate monomer, and first initiator;
c) combining the first and second solutions to provide the first mixture of the method.

In some embodiments of the method, the first and second solutions of the method are formed with approximately the same concentration of first and second monomer, respectively. The percentage of each component can then be varied by adjusting the amounts each solution used to form the first mixture.

In some embodiments, the first mixture can be formed on a surface of an electrode. For example, each component, or a combination of one or more components, can be individually deposited to form the mixture. Similarly, when the mixture is formed by combining individual solutions, the solutions can be combined on a surface of an electrode to form the mixture.

In embodiments where the second mixture includes the second methacrylate monomer, the second mixture can be formed on the sensing layer. For example, each component, or a combination of one or more components, can be individually deposited onto the sensing layer to form the second mixture.

The first methacrylate monomer can be the modified glucose described above. That is, the first methacrylate can be covalently bound to glucose oxidase through a hydrophilic linker. In some embodiments, the first methacrylate monomer can be a modified glucose having the structure of any of formulae (I) or (Ia)-(Ic).

The second methacrylate monomer can have hydrophilic side chains that can have one or more heteroatoms. In certain embodiments, the side chains are selected to form the crosslinked, hydrophilic copolymer of the glucose sensor as described herein.

In some embodiments of the method, the second methacrylate monomer can have the structure of formula (V):

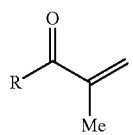

(V)

where R is a hydrophilic group. In certain embodiments of the method, the hydrophilic group includes one or more hydroxy groups, such as an alcohol.

In some embodiments of the method, the second methacrylate monomer has the structure of formula (Va):

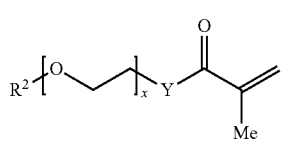

(Va)

where Y, x and $R^2$ are selected to provide the third methacrylate-derived monomeric unit of the sensing layer or protective membrane, as described herein.

In certain embodiments of the method, the second methacrylate monomer has the structure:

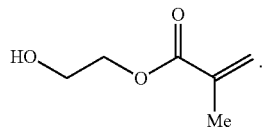

The first and/or second dimethacrylate monomer is a molecule having two terminal methacrylate groups tethered by a hydrophilic linker. The hydrophilic linker is selected to provide the crosslinks between the second or fourth methacrylate-derived units in different backbone chains of the sensing layer or protective membrane, respectively, as described herein.

The extent of crosslinking in the sensing layer or protective membrane of the glucose sensor can be controlled by adjusting the amount of first and/or second dimethacrylate monomer in the first or second mixture used to form the sensing layer and/or protective membrane, respectively. In some embodiments, the first and/or second dimethacrylate monomer is about 0.1% to about 15% of the mixture. In other examples, the amount is about 1% to about 5%, or about 5% to about 10%, or about 10% to about 15% of the mixture. In some embodiments, the amount is about 1%. In some instances, the first and second mixtures include about 1% of the first and second dimethacrylate monomer, respectively.

In some embodiments of the method, the first and/or second dimethacrylate monomer includes one or more alkylene oxide units to provide the crosslinks of the sensing layer and/or protective membrane as described herein. In some embodiments, the first and/or second dimethacrylate monomer includes poly(ethylene oxide). For example, the dimethacrylate monomer can have the structure of formula (VI):

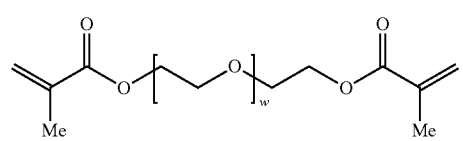

(VI)

where w is 1, 2, 3, 4, 5, 6, 7, 8, 9 or 10.

In other embodiments of the method, the first and/or second dimethacrylate monomer can have the structure of formula (VI) where w is such that the number average molecular weight ($M_n$) of the PEG portion of the dimethacrylate monomer is about 100 to about 10,000. For example, w can be selected such that the $M_n$ of the PEG portion of dimethacrylate monomer falls within a range in Table 3. In some embodiments, the dimethacrylate monomer is di(ethylene glycol) dimethacrylate.

Depositing the mixture of sensing layer components onto a surface of an electrode, or the mixture of protective membrane components onto the cured sensing layer can be accomplished by a number of methods. For example, the depositing can be performed manually with a micro-syringe, or by automated fabrication processes with nano-jet dispensing equipment.

In some embodiments of the method, the amount of the first mixture and/or the second mixture is selected to provide the desired thickness of the crosslinked, hydrophilic copolymer of the glucose sensor. In some embodiments, the amount deposited on the electrode and/or the cured sensing layer is about 50 nL/mm² to about 500 nL/mm². In other examples, the amount is about 50 μm to about 150 μm, or about 150 μm to about 300 μm, or about 300 μm to about 500 μm in thickness. In some embodiments, the amount is about 100 nL/mm². In some instances, depositing about 100 nL/mm² of a mixture including the first and second monomers provides a crosslinked, hydrophilic copolymer that is about 20 μm in thickness. In other embodiments, depositing about 20 nL/mm² of the first mixture, followed by depositing about 40 nL/mm² of a the second mixture provides a sensing layer and protective membrane with a combined thickness of about 20 μm.

Conditions suitable to initiate polymerization (i.e., curing) can be selected based on the characteristics of the initiator and the monomers being polymerized, but not to degrade the glucose oxidase. For example, the temperature and pH of the method can be selected to preserve the activity of the glucose oxidase. In certain embodiments the initiator is activated with ultraviolet (UV) light. For example, when 2,2-dimethoxy-2-phenylacetophenone is used as an initiator, the curing can be performed with ultraviolet light.

EXAMPLES

Example 1. Synthesis of Bifunctional Cross Linkers

Methacrylate PluronicF38

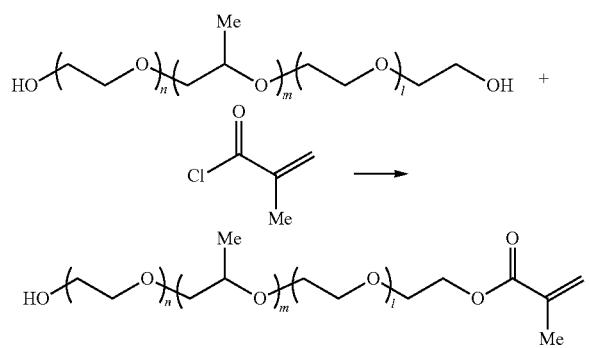

PluronicF38 (5 g) was dissolved in anhydrous toluene (20 ml) under nitrogen and magnetic stirring. Triethylamine (221 μl, 1.6 mmol) was added. Methacryloyl chloride (87 μl, 1.2 mmol) was added slowly at 0° C. under nitrogen. The mixture was stirred for 2 h at 0° C., sealed and left under stirring for 24 h at room temperature. Side product triethylamine hydrochloride was removed by filtration. The crude product was purified by re-dissolving in tetrahydrofuran and precipitating in ethyl ether several times, followed by preparative chromatography. The final product was dried under vacuum at 25° C. for 24 hours. Yields: ~30%. ¹HNMR (CDCl₃): δ 6.25 (s, 1H, gem C=C), 5.78 (s, 1H, gem C=C), 4.28 (m, 2H, OCH₂), 3.36-3.79 (m, 368H, —OCH₂CH₂O—, —OCHMeCH₂—), 1.95 (s, 3H, Me), 1.16 (d, 48H, Me).

Methacrylate-PluronicF38-Succinimidyl Carbonate

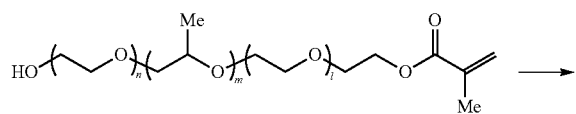

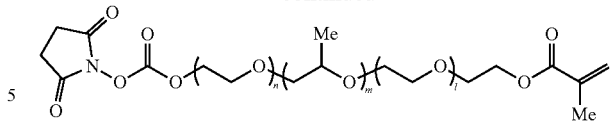

Methacrylate PluronicF38 (2 g, 0.4 mmol) and N,N'-Disuccinimidyl carbonate (1.0 g, 4 mmol) were dissolved in anhydrous dichloromethane (20 ml). Anhydrous pyridine (1 ml) was added at 0° C. under nitrogen. The reaction mixture was stirred under nitrogen at ambient temperature for 6 hours. The reaction mixture was filtered to remove any solid. The dichloromethane and pyridine in filtrate were removed under reduced pressure. The resulting residue was precipitated in DCM/Ether for several times to yield crude product 1.5 g. The crude product was used for enzyme conjugation without further purification, but a small amount of product was purified for characterization. ¹HNMR (CDCl₃): δ 6.21 (s, 1H, gem C=C), 5.52 (s, 1H, gem C=C), 4.48 (t, 2H), 4.31 (t, 2H), 3.36-3.85 (m, 368H, —OCH₂CH₂O—, —OCHMeCH₂—), 2.84 (S, 4H, Succinimidyl), 1.93 (s, 3H, Me), 1.18 (d, 48H, Me).

Methacrylate-PEG360-Succinimidyl Carbonate

Methacrylate-PEG360-Succinimidyl Ester was synthesized by following the same procedure described above, replacing Metacrylate-PluronicF38 with poly(ethylene glycol) methacrylate.

Example 2. Glucose Oxidase Modification

Methacrylate-PluronicF38-GOx

Glucose oxidase (300 mg) was washed with 10 mM MES buffer (pH 5.8) by using 30K Amicon Tube (Millipore) and centrifuge at 4° C. (12 ml×2). The buffer was then changed to 100 mM HEPES (pH 8.5) as 25 mg/ml GOx solution. A 50 μl aliquot of solution was removed for reference in the of degree of modification analysis. To the GOx solution, Methacrylate-PluronicF38-Succinimidyl Ester (600 mg) was added and mixed well in the vessel. The reaction vessel was placed on a shaker at room temperature for 1 hour. The reaction was kept away from light to prevent polymerization. The reaction mixture was mixed into 100 ml of 10 mM MES (pH 5.8) buffer. The conjugated GOx was isolated by centrifugation using 100K Amicon tube, and further purified with washing with 10 mM MES (15 ml×3). Finally the solution in 10 mM MES buffer was distributed into glass vials, 5 mg/vial. Lyophilization gave product as pale yellow powder. The product can be stored at −20° C. for up to 3 months.

Methacrylate-PEG360-GOx

The conjugate of Methacrylate-PEG360-GOx was synthesized by following the same procedure described above, replacing Methacrylate-PluronicF38-Succinididyl Ester with Methacrylate-PEG360-Succinididyl Ester.

Example 3. Characterization of GOx Conjugates

Degree of Modification

Degree of modification was determined by colorimetric titration on the non-conjugated amino groups before and after conjugation. 2,4,6-trinitrobenzene sulfonic acid was used to quantify the free amino groups by reacting with primary amines to form a highly chromogenic derivative, which can be measured at 335 nm. The native glucose oxidase used as reference was washed with buffer using 30K Amicon tube to remove free amino acids and peptides. The degree of modification was calculated by ratio of molar amount of primary amine of modified GOx to that of native GOx. The results are listed in Table 4.

Activity of Modified Glucose Oxidase

The activity assays were performed after conjugation, and the data were compared with that of native glucose oxidase. To reach the high assay sensitivity a fluorometric method was used. The glucose oxidase catalyzes the oxidation of beta-D-glucose into hydrogen peroxide and D-glucono-1,5-lactone, which is hydrolyzed to gluconic acid. Amplite™ can be oxidized by the hydrogen peroxide and form a fluorescent substance. The fluorescent signal can be recorded at Ex/Em=540/590 nm. The assay was carried out on 96-well micro plate; the LOD of the assay was 0.05 mU/ml. The retained GOx activity was calculated by the ratio of activity of modified GOx to that of native GOx. The results are listed in Table 4.

TABLE 4

Degree of Modification and GOx Activity of PluronicF38-GOx

| Modified GOx | Degree of Modification (%) | Retained GOx Activity % |
|---|---|---|
| Methacrylate-PluronicF38-GOx | 35-65% | 60-90% |
| Methacrylate-PEG360-GOx | 64% | 71% |

Example 4. Immobilization of Glucose Oxidase and Membrane Performance Formation of GOx Hydrogel Membrane Hydrogel membranes were formed by photo-induced polymerization of a formulation containing of 2-hydroxyethyl methacrylate (HEMA), 3-Sulfopropyldimethyl-3-methacrylamidopropylammonium (12), diethylene glycol dimethacrylate (DEGDMA; crosslinker) and 2,2'-Dimethoxy-2-phenylacetophenone (initiator). To compare membrane performance made by native GOx and modified GOx, three formulations were prepared (Table 5) and tested on solubility, amperometric response to glucose concentration, and GOx leach rate from the membranes.

TABLE 5

GOx Hydrogel Formulations

| | GOx | 10 mM PBS | HEMA (with 1% DEGDMA and 1% initiator) | I2 |
|---|---|---|---|---|
| A | Native GOx | 250 µl | 225 µl | 37.5 mg |
| B | Methacrylate-PluronicF38-GOx | 250 µl | 225 µl | 37.5 mg |
| C | Methacrylate-PEG360-GOx | 250 µl | 225 µl | 37.5 mg |

Determination of GOx Release from Hydrogel Membrane

GOx activity assay was used to monitor the GOx release from the hydrogel membrane. One piece of GOx-Hydrogel membrane on PET was submerged in 1 ml of 10 mM phosphate buffer saline (PBS, pH 7.4) with shaking. The activity assay was performed on the aliquot of 10 µl extracting solution at 1, 3, 6 and 24 hours. The percentage of GOx release was calculated by the GOx activity determined in the extracting solution over the total activity in the GOx-hydrogel membrane. The results are presented in FIG. 1.

Response to Glucose Concentration

Figure 2:
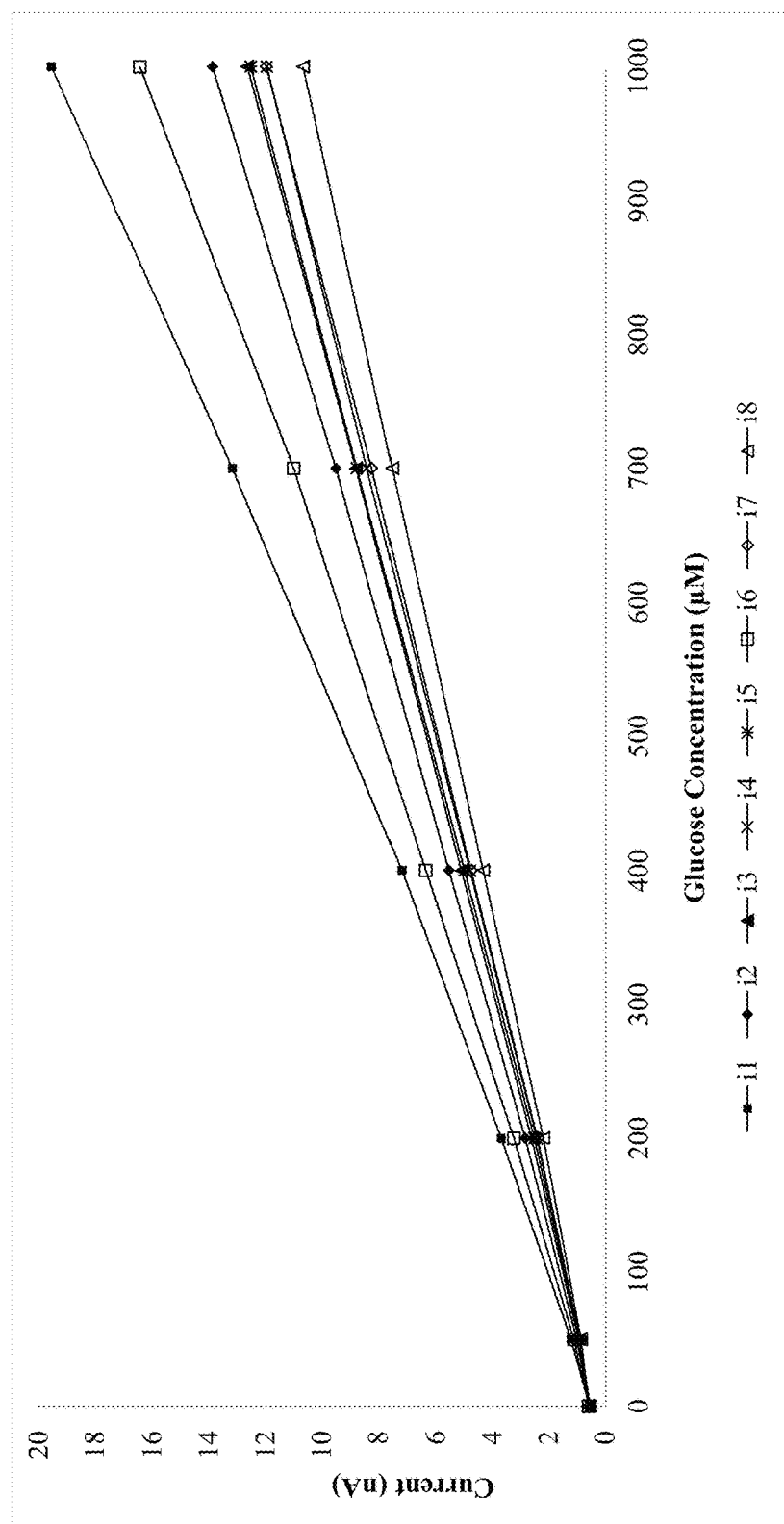
FIG. 2 shows the amperometric response to glucose concentration of eight (8) different sensors having a hydrogel membrane made with Native GOx.
Figure 3:
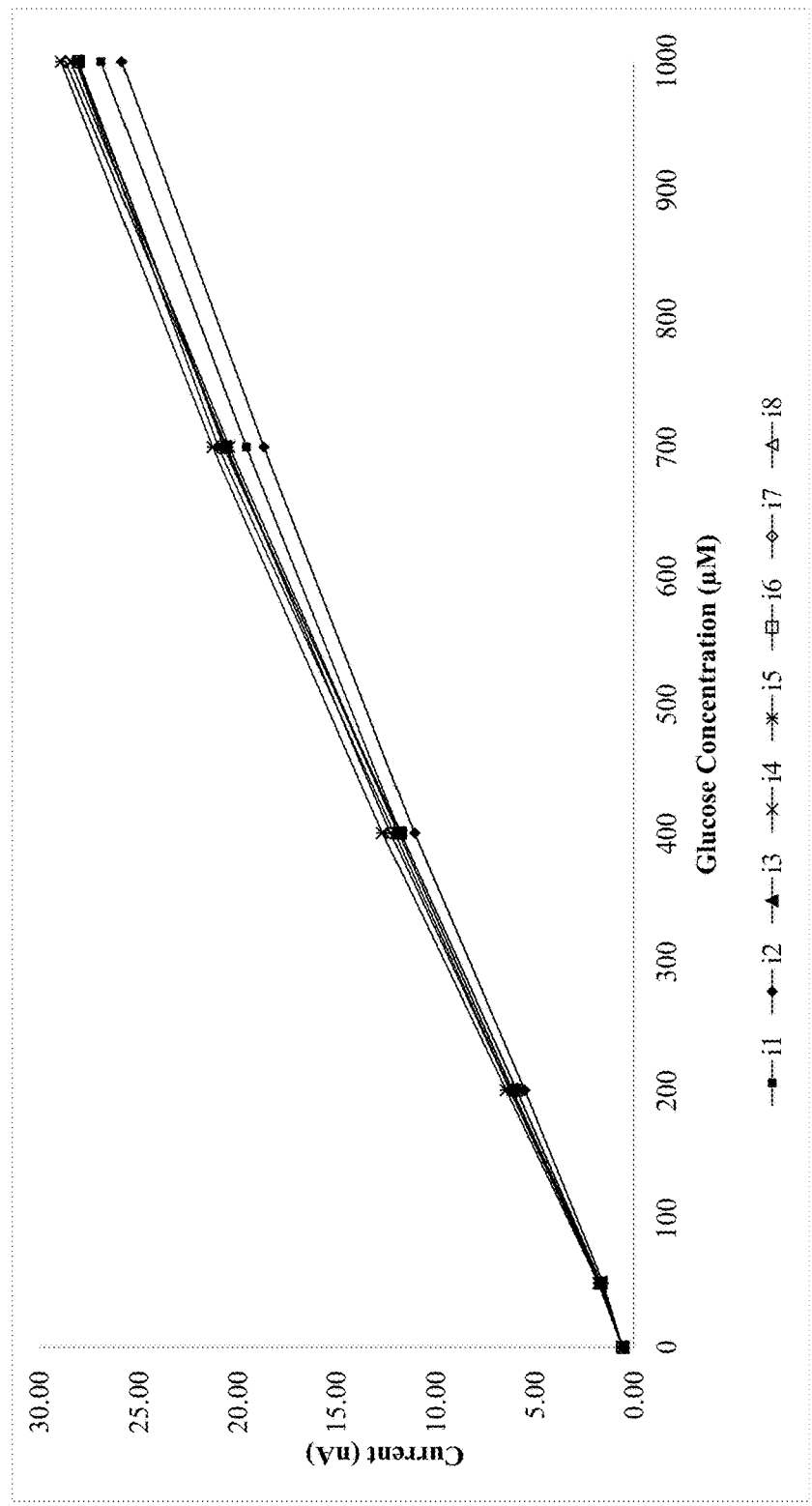
FIG. 3 shows the amperometric response to glucose concentration of eight (8) different sensors having a hydrogel membrane made with Methacrylate-PluronicF38-GOx.
Figure 4:
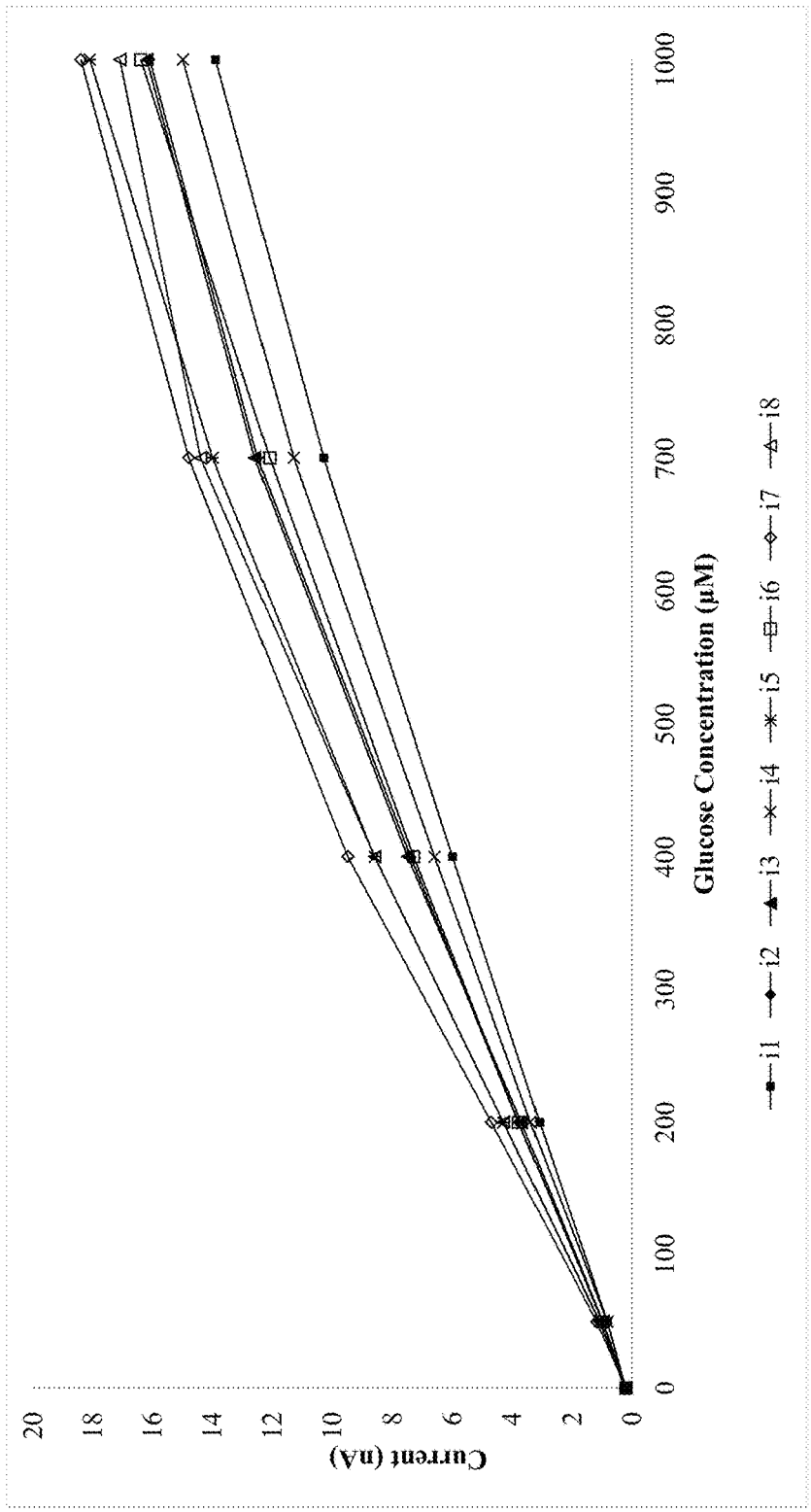
FIG. 4 shows the amperometric response to glucose concentration of eight (8) different sensors having a hydrogel membrane made with Methacrylate-PEG360-GOx.

Three electrochemical sensors were made, 1) with a native GOx, 2) with Methacrylate-PluronicF38-GOx and 3) with Methacrylate-PEG360-GOx modified GOx membranes. The sensors were tested in a PBS buffer at different glucose concentrations. At each glucose concentration, the amperometric current in nanoamperes (nA) was recorded. The results are presented in FIGS. 2-4.

Although the crosslinked, hydrophilic copolymers in the above examples include methacrylate groups, there are a number of ethylenically unsaturated groups known in the art to be capable of undergoing polymerization. Ethylenically unsaturated monomers and macromers may be either acrylic- or vinyl-containing. Vinyl-containing monomers contain the vinyl grouping ($CH_2$=CH—), and are generally highly reactive. Acrylic-containing monomers are represented by the formula:

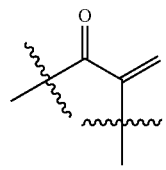 [SMILES: *C(=C)C(*)=O]

Examples of suitable polymerizable groups may include acrylic-, ethacrylic-, itaconic-, styryl-, acrylamido-, methacrylamido- and vinyl-containing groups such as the allyl group.

In addition to the above disclosed methods of forming crosslinked, hydrophilic copolymers by the polymerization of ethylenically unsaturated monomers and macromonomers, additional chemistries will be known to one or ordinary skill in the art to from such copolymers. As an example, epoxy chemistry, in which multifunctional amines and multifunctional epoxy compounds are mixed together and cured, can be used to form crosslinked, hydrophilic copolymers. Additionally, urethane chemistry may be used, in which multifunctional isocyanates are mixed with multifunctional alcohols and cured to provide crosslinked, hydrophilic copolymers. Other chemistries for the formation of crosslinked, hydrophilic copolymers exist, and will be well known to those of ordinary skill in the art.

It should be understood that arrangements described herein are for purposes of example only. As such, those skilled in the art will appreciate that other arrangements and other elements (e.g., machines, interfaces, functions, orders, and groupings of functions, etc.) can be used instead, and some elements can be omitted altogether according to the desired results. Further, many of the elements that are described are functional entities that can be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

The invention claimed is:

1. A modified glucose oxidase comprising a glucose oxidase wherein at least one amino group is substituted with a methacrylate through a hydrophilic linker comprising at least one ethylene or propylene oxide unit.

2. The modified glucose oxidase of claim 1, wherein the linker comprises at least one ethylene oxide unit.

3. The modified glucose oxidase of claim 1, having the structure of formula (Ia):

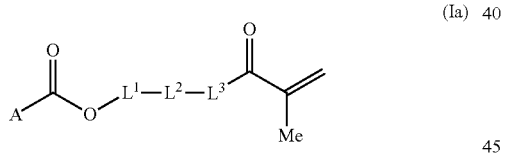

(Ia)

wherein
each of $L^1$, $L^2$ and $L^3$ can be independently absent or an alkylene oxide unit, wherein at least one of $L^1$, $L^2$ and $L^3$ is an ethylene or propylene oxide unit;
$R^1$ is hydrogen or $C_1$-$C_6$alkyl; and
A is glucose oxidase.

4. The modified glucose oxidase of claim 1, having the structure of formula (Ib):

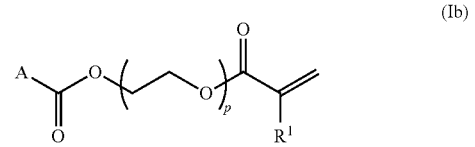

(Ib)

wherein
p is 1-100;
$R^1$ is hydrogen or —$C_1$-$C_6$alkyl; and
A is glucose oxidase.

5. The modified glucose oxidase of claim 4, wherein the $M_n$ of the poly(ethylene oxide) portion of the modified glucose falls within the range of 300 to 400.

6. The modified glucose oxidase of claim 1, having the structure of formula (Ic):

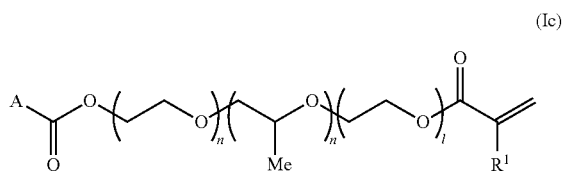

(Ic)

wherein
n is 1-50;
m is 1-100;
l is 1-50;
$R^1$ is hydrogen or —$C_1$-$C_6$alkyl; and
A is glucose oxidase.

7. The modified glucose oxidase of claim 6, wherein n is 10-20; m is 30-50; and l is 1-50.

8. The modified glucose oxidase of claim 6, wherein the combined $M_n$ of the poly(ethylene oxide) and poly(propylene oxide) portion of the modified glucose falls within the range of about 4,000 g/mol to about 5,000 g/mol.

9. A method for making the modified glucose oxidase of claim 1, the method comprising reacting glucose oxidase with an activated methacrylate, wherein the methacrylate is bound through a linker comprising at least one ethylene or propylene oxide unit to a reactive group capable of forming a covalent bound to glucose oxidase.

10. A glucose sensor comprising:
a sensing layer in contact with a surface of an electrode, wherein the sensing layer comprises:
backbone chains comprising
first methacrylate-derived monomeric units, each of which is covalently bound to a primary amino group on glucose oxidase through a hydrophilic linker comprising at least one ethylene or propylene oxide unit,
second methacrylate-derived monomeric units, and
optionally, third methacrylate-derived monomeric units, each having a hydrophilic side chain,
hydrophilic crosslinks between the second methacrylate-derived units in different backbone chains; and
optionally an additional layer provided on the sensing layer comprising third methacrylate-derived monomeric units, each having a hydrophilic side chain,
wherein the third methacrylate-derived monomeric units are present in at least one of the additional layer or the backbone chains of the sensing layer.

11. The sensor of claim 10, wherein the third methacrylate-derived monomeric units are present in the backbone chains of the sensing layer.

12. The sensor of claim 10, wherein the third methacrylate-derived monomeric units are present in an additional layer, wherein the additional layer is a protective membrane comprising:
backbone chains comprising:
third methacrylate-derived monomeric units, each unit having a hydrophilic side chain; and
fourth methacrylate-derived monomeric units; and
hydrophilic crosslinks between the fourth methacrylate-derived units in different backbone chains.

13. The sensor of claim 10, wherein the first methacrylate-derived monomeric units have the structure of formula (IIa):

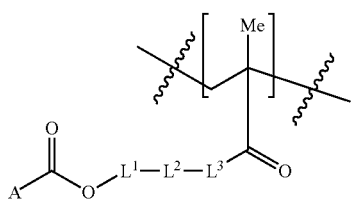

(IIa)

wherein
  each of L¹, L² and L³ can be independently absent or an ethylene or propylene oxide unit, wherein at least one of L¹, L² and L³ is an ethylene or propylene oxide unit; and
  A is glucose oxidase.

14. The sensor of claim 10, wherein the first methacrylate-derived monomeric units have the structure of formula (IIb):

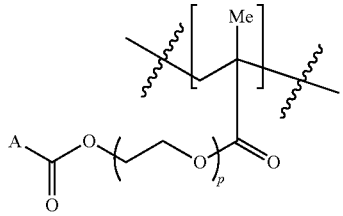

(IIb)

wherein
  p is 1-100; and
  A is glucose oxidase.

15. The sensor of claim 10, wherein the first methacrylate-derived monomeric units have the structure of formula (IIc):

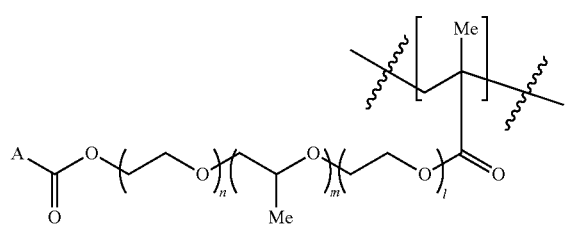

(IIc)

wherein
  n is 1-50;
  m is 1-100;
  l is 1-50; and
  A is glucose oxidase.

16. The sensor of claim 10, wherein the third methacrylate-derived units have the structure of formula (IIIa):

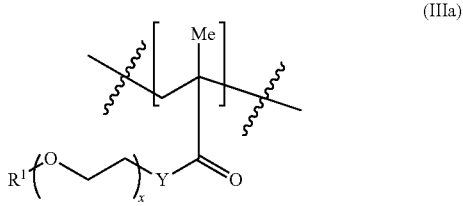

(IIIa)

wherein
  Y is —O—, —NR'— or —S—;
  x is 1-10; and
  R¹ is hydrogen, —C₁-C₁₂alkyl, —C₁-C₁₂alkyl-OH, —SiR'₃, —C₁-C₁₂alkyl-C(O)OR', wherein R' is hydrogen or —C₁-C₁₂alkyl.

17. The sensor of claim 10, wherein the third methacrylate-derived units have the structure:

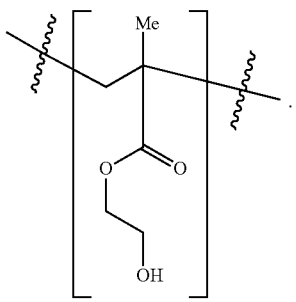

18. The sensor of claim 12, wherein the hydrophilic crosslinks between the second or fourth methacrylate-derived units in different backbone chains are derived from the di(ethylene oxide) portion of di(ethylene glycol) dimethacrylate.

19. The sensor of claim 10, wherein the sensing layer comprises:
  first methacrylate-derived monomeric units having the structure of formula (IIb):

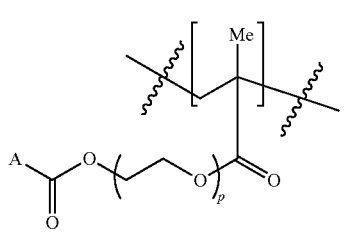

(IIb)

wherein
  the $M_n$ of the poly(ethylene oxide) portion of formula (IIb) falls within the range of 300 to 400; and
  A is glucose oxidase;
third methacrylate-derived monomeric units having the structure:

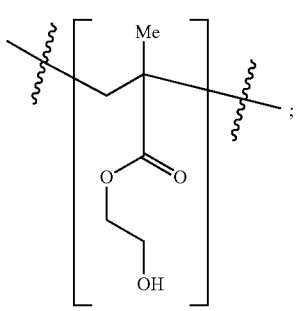

and
crosslinks between the second methacrylate-derived units in different backbone chains derived from the di(ethylene oxide) portion of di(ethylene glycol) dimethacrylate.

20. The sensor of claim 10, wherein the sensing layer comprises:
first methacrylate-derived monomeric units having the structure of formula (IIc):

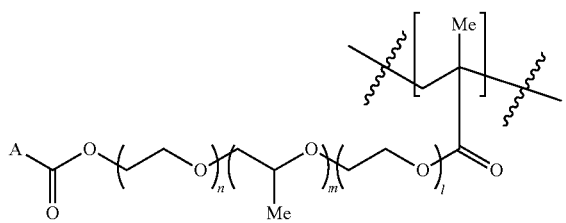

(IIc)

wherein
n is 10-20;
m is 30-50;
l is 1-50; and
A is glucose oxidase;
third methacrylate-derived monomeric units having the structure:

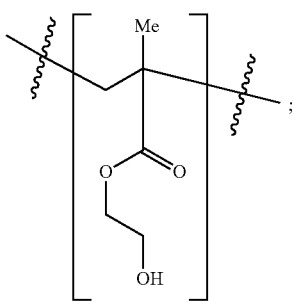

and
crosslinks between the second methacrylate-derived units in different backbone chains derived from the di(ethylene oxide) portion of di(ethylene glycol) dimethacrylate.

* * * * *